(12) United States Patent
Sakagami et al.

(10) Patent No.: US 8,328,730 B2
(45) Date of Patent: Dec. 11, 2012

(54) LIVING BODY MEASUREMENT APPARATUS

(75) Inventors: Toshimasa Sakagami, Tokyo (JP);
Hiroshi Karasuno, Tokyo (JP); Hisashi Kuroda, Tokyo (JP); Makoto Sasaki, Tokyo (JP); Wataru Orito, Tokyo (JP)

(73) Assignee: ITO Co., Ltd., Tokyo (JP)

( * ) Notice: Subject to any disclaimer, the term of this patent is extended or adjusted under 35 U.S.C. 154(b) by 0 days.

(21) Appl. No.: 12/663,794

(22) PCT Filed: Oct. 15, 2007

(86) PCT No.: PCT/JP2007/070100
§ 371 (c)(1),
(2), (4) Date: Dec. 9, 2009

(87) PCT Pub. No.: WO2008/152751
PCT Pub. Date: Dec. 18, 2008

(65) Prior Publication Data
US 2010/0174208 A1  Jul. 8, 2010

(30) Foreign Application Priority Data

Jun. 13, 2007 (JP) ................................ 2007-156380

(51) Int. Cl.
*A61B 19/00* (2006.01)
*A61B 5/103* (2006.01)
*A61B 5/117* (2006.01)
*G01N 3/48* (2006.01)

(52) U.S. Cl. ............. 600/557; 600/553; 600/587; 73/81

(58) Field of Classification Search .................. 600/557, 600/550, 552–553, 587; 73/81–82
See application file for complete search history.

(56) References Cited

U.S. PATENT DOCUMENTS 5,027,828 A * 7/1991 Kovacevic et al. ............ 600/587
(Continued)

FOREIGN PATENT DOCUMENTS

JP       57-179407       11/1982
(Continued)

OTHER PUBLICATIONS

International Search Report dated Oct. 26, 2007, for corresponding Patent Application PCT/JP2007/070100.

(Continued)

*Primary Examiner* — Jeffrey G Hoekstra
*Assistant Examiner* — H. Q. Nguyen
(74) *Attorney, Agent, or Firm* — K&L Gates LLP

(57) ABSTRACT

A living body measurement apparatus according to the present invention functions both as a muscular tissue hardness tester for measuring hardness of muscular tissue of a living body and as an algesiometer for measuring a degree of sense of pain of the living body, and the apparatus includes: an contacting section which includes a first contact surface contacting the living body, and which applies pressure to the living body; an auxiliary section which includes a second contact surface contacting the living body, and which supports the second contact surface so that the second contact surface perform reciprocating movement between a coplanar position in which the second contact surface is disposed substantially coplanar with the first contact surface and a retracted position in which the second contact surface is retracted with respect to the first contact surface; and a locking mechanism which locks the auxiliary section in a state in which the second contact surface is disposed at the retracted position.

6 Claims, 6 Drawing Sheets

U.S. PATENT DOCUMENTS

| | | |
|---|---|---|
| 5,879,312 A | 3/1999 | Imoto |
| 6,063,044 A | 5/2000 | Leonard et al. |

FOREIGN PATENT DOCUMENTS

| | | |
|---|---|---|
| JP | 61-205507 | 9/1986 |
| JP | 2046321 | 2/1990 |
| JP | 06-090240 | 3/1994 |
| JP | 06090240 | 3/1994 |
| JP | 06-313752 | 11/1994 |
| JP | 10-085191 | 4/1998 |
| JP | 10-179524 | 7/1998 |
| JP | 2000-316818 | 11/2000 |
| JP | 2006-329935 | 12/2006 |
| WO | 2008-136140 | 11/2008 |
| WO | 2008-152751 | 12/2008 |

OTHER PUBLICATIONS

Notice of Office Action from Korean Intellectual Property Office dated Mar. 15, 2011.

Japanese Patent Office, Office Action issued in connection with Japanese Application Serial No. 2007-156380 drafted Dec. 28, 2011, mailed Jan. 4, 2012. (5 pages).

* cited by examiner

LIVING BODY MEASUREMENT APPARATUS

TECHNICAL FIELD

The present invention relates to a living body measurement apparatus for measuring hardness of muscular tissue and a degree of sense of pain of a living body.

Priority is claimed on Japanese Patent Application No. 2007-156380, filed Jun. 13, 2007, the content of which is incorporated herein by reference.

BACKGROUND ART

A muscular tissue hardness tester for measuring hardness of muscular tissue by applying pressure to a living body has been used.

Such a muscular tissue hardness tester includes a main needle which is made to contact a living body and a sub-cylinder which covers the main needle (see, for example, Patent Document 1). The sub-cylinder is provided to move forward and backward with respect to the main needle and is always urged by an urging member toward a tip.

With this configuration, skin around a site subject to measurement is pressed by a distal end surface of the sub-cylinder and the main needle is pushed into the skin. The pressure of the main needle at this time is measured to determine hardness of the muscular tissue of the living body.

An algesiometer for measuring a degree of sense of pain of a living body by applying pressure to the living body has been used. In such an algesiometer, a main needle is made to contact skin of a subject and is pushed against the skin with increasing pressure. The subject is asked to tell when he or she feels pain. The pressure of the main needle at this time is measured to determine the degree of sense of pain of the living body.

[Patent Document 1] Japanese Unexamined Patent Application, First Publication No. H10-179524

DISCLOSURE OF INVENTION

Problem To Be Solved By the Invention

The muscular tissue hardness tester and the algesiometer described above are provided separately. Accordingly, if these two devices are used at a time, there is a problem that the control burden of the devices is increased.

For example, even if the muscular tissue hardness tester disclosed in Patent Document 1 is used as an algesiometer, there is a problem that the degree of sense of pain cannot be measured accurately. This is because it is necessary to press the vicinity of the subject site by the sub-cylinder to measure hardness of the muscular tissue. When measuring the degree of sense of pain, however, it is necessary to press a small area by only a distal end surface of the main needle in order to determine the site where the subject feels pain.

The invention is made in view of the circumstance described above. An object of the invention is to provide a living body measurement apparatus with which hardness and a degree of sense of pain of muscular tissue can be measured easily and highly accurately in a single device.

Means For Solving the Problem

In order to solve the aforementioned problems, the invention provides the following means.

A living body measurement apparatus according to the present invention functions both as a muscular tissue hardness tester for measuring hardness of muscular tissue of a living body, and as an algesiometer for measuring a degree of sense of pain of the living body, and the apparatus includes: an contacting section which includes a first contact surface contacting the living body, and which applies pressure to the living body; an auxiliary section which includes a second contact surface contacting the living body, and which supports the second contact surface so that the second contact surface perform reciprocating movement between a coplanar position in which the second contact surface is disposed substantially coplanar with the first contact surface and a retracted position in which the second contact surface is retracted with respect to the first contact surface; and a locking mechanism which locks the auxiliary section in a state in which the second contact surface is disposed at the retracted position.

With this configuration, the second contact surface can be held at the retracted position by locking the auxiliary section with the locking mechanism.

The living body measurement apparatus according to the present invention may further include a support section which supports the auxiliary section so that the second contact surface performs the reciprocating movement and the locking mechanism may include: a first elongated groove which is formed in either one of the auxiliary section and the support section, and which extends in a reciprocating direction of the reciprocating movement of the second contact surface; a second elongated groove which is formed in the one of the auxiliary section and the support section, and which extends from the first elongated groove in a direction perpendicular to the reciprocating direction; and a protruding portion which is formed in the other of the auxiliary section and the support section, and which is disposed at either one of the first elongated groove and the second elongated groove.

With this configuration, the auxiliary section can be securely locked by a simple structure.

The living body measurement apparatus may further include: a response operating section which outputs a response signal; a reporting section which reports output of the response signal; and a control section which performs control of driving the reporting section when the response signal is input from the response operating section.

With this configuration, the degree of sense of pain of the subject can be measured with high accuracy.

In the living body measurement apparatus according to the present invention, the contacting section may be replaceable.

With this configuration, an optimal contacting section in accordance with the state of the subject site can be attached to thereby make it possible to perform a more accurate measurement.

Effect of the Invention

According to the invention, the second contact surface can be held at the retracted position by locking the auxiliary section with the locking mechanism. Thus, hardness of the muscular tissue and the degree of sense of pain can be measured easily and highly accurately with a single device.

REFERENCE SYMBOLS

1 Living body measurement apparatus
6 Display section (reporting section)
10 Response switch (response operating section)
16 Support cylinder (support section)
26 Auxiliary cylinder (auxiliary section)
26a Distal end surface (second contact surface)
22 Protruding portion (protruding portion, locking mechanism)
32 First elongated groove (locking mechanism)
33 Second elongated groove (locking mechanism)
40 Tip (contacting section)
40a Distal end surface (first contact surface)
57 Control section
P1 Coplanar position
P2 Retracted position

BEST MODE FOR CARRYING OUT THE INVENTION

Hereinafter, a living body measurement apparatus according to an embodiment of the invention will be described with reference to the drawings.

Figure 1:
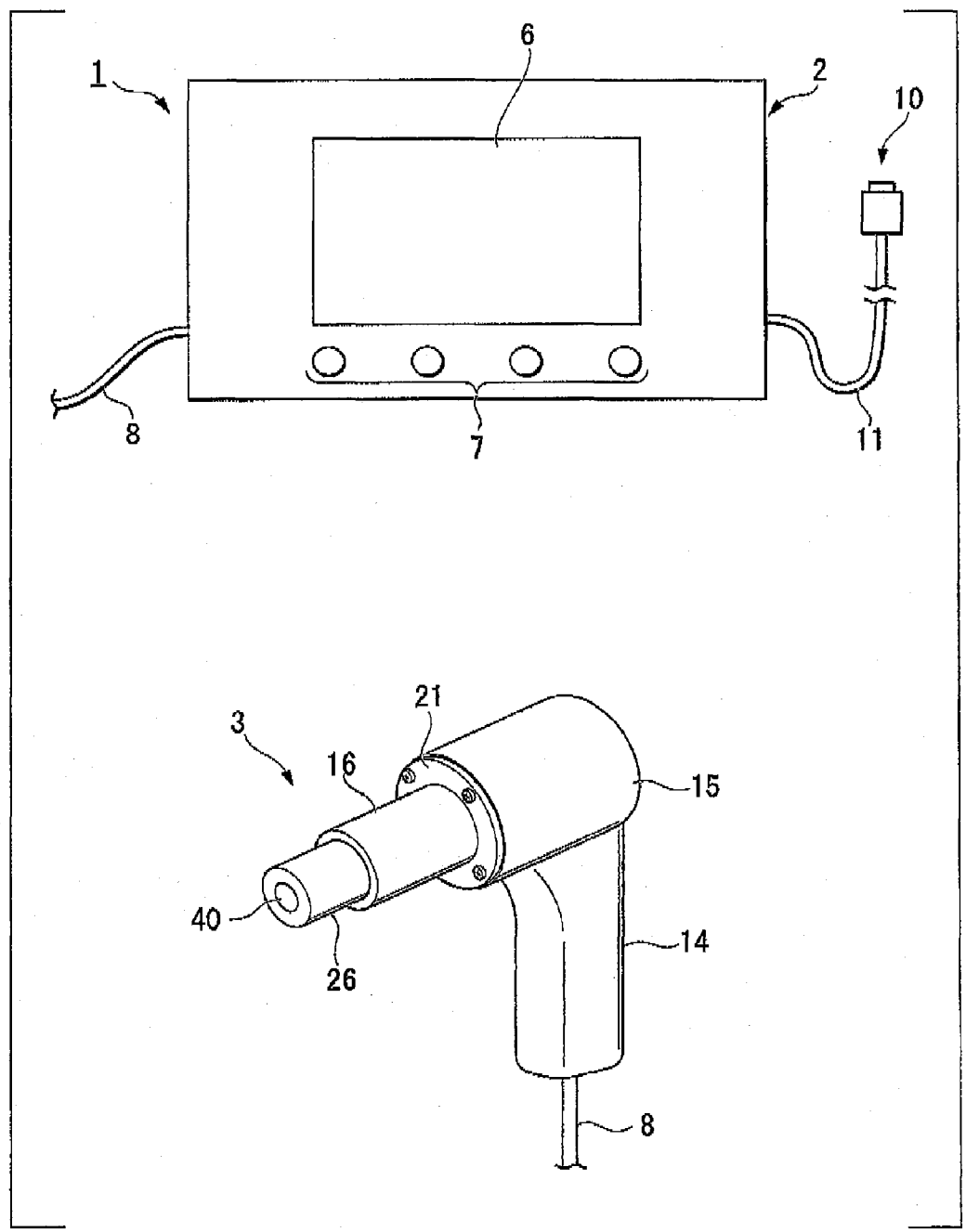
FIG. 1 is an overall structural view illustrating an embodiment of a living body measurement apparatus according to the invention.

FIG. 1 illustrates a living body measurement apparatus as an embodiment of the invention.

A living body measurement apparatus 1 includes a rectangular parallelepiped-shaped device main body 2 and a probe 3 connected to the device main body 2 via a cable 8.

A rectangular-shaped display section (reporting section) 6 for displaying various information is provided on a top panel of the device main body 2.

The display section 6 may be a liquid crystal display, for example.

A main body operation section 7 for execution of various operations is provided on the top panel of the device main body 2.

A response switch (response operating section) 10 which can switch between turning on and off is connected with the device main body 2 via a cable 11. When not pressed, the response switch 10 is kept off and outputs no response signals. When pressed, the response switch 10 is turned on and outputs response signals.

The probe 3 includes a holding section 14 held by a user. The holding section 14 has an elongated rectangular parallelepiped shape. A bottomed cylindrical probe main body 15 is provided at an end portion of the holding section 14. The probe main body 15 is formed integrally with the holding section 14.

An axial direction of the probe main body 15 intersects the longitudinal direction of the holding section 14, A cylindrical support cylinder (support section) 16 is provided at an open end of the probe main body 16. A base end flange 21 having the same diameter as that of the open end of the probe main body 15 is provided at a base end of the support cylinder 16. The base end flange 21 extends in a radial direction toward the outside of the support cylinder 16. The base end flange 21 of the support cylinder 16 is provided to cover the open end of the probe main body 15.

Figure 2:
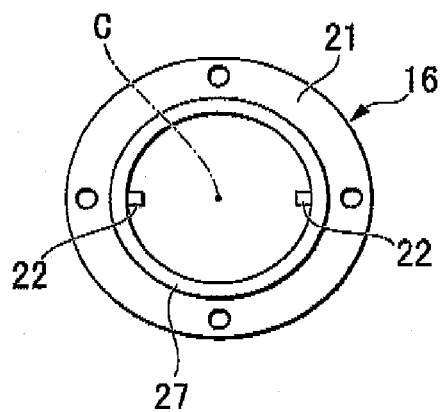
FIG. 2 is a front view illustrating a support section of the living body measurement apparatus illustrated in FIG. 1.

As illustrated in FIG. 2, a pair of protruding portions (protrusion, or locking mechanism) 22 are provided to protrude in a radial direction toward the inside on an inner circumferential surface of the support cylinder 16. The protruding portions 22 oppose each other with a central portion C of the support cylinder 16 disposed therebetween.

Figure 3:
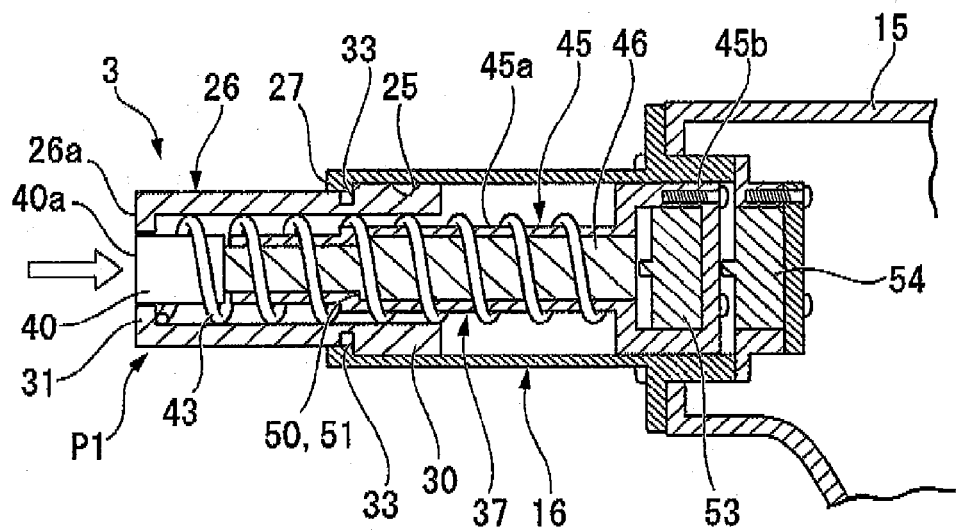
FIG. 3 is a lateral cross-sectional view illustrating a part of a probe of the living body measurement apparatus illustrated in FIG. 1.

As illustrated in FIG. 3, a tip flange 27 is provided at the end portion of the support cylinder 16 so as to extend in a radial direction toward the inside of the support cylinder 16.

Figure 4:
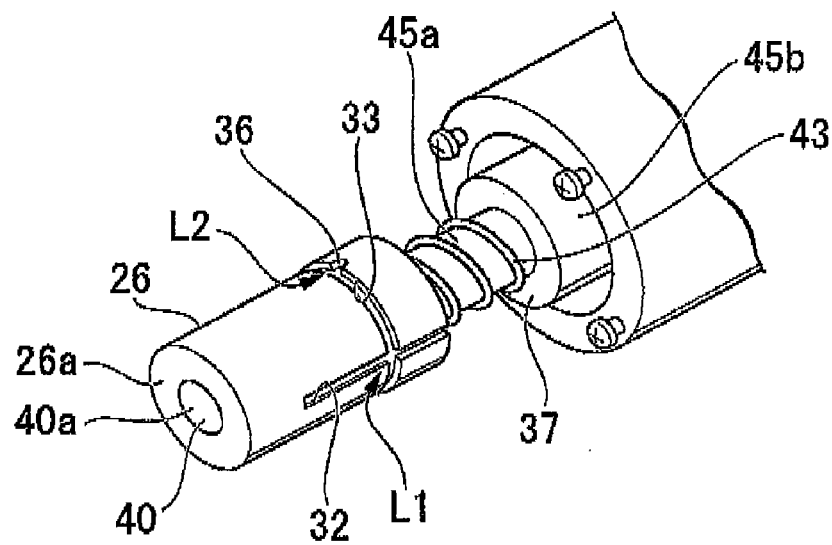
FIG. 4 is a perspective view illustrating an auxiliary cylinder of the living body measurement apparatus illustrated in FIG. 1.

A cylindrical auxiliary cylinder (auxiliary section) 26 is inserted in a cylinder hole 25 of the support cylinder 16. As illustrated in FIG. 4, a pair of first elongated grooves (locking mechanism) 32 extending in a longitudinal direction of the auxiliary cylinder 26 are provided on an outer circumferential surface of the auxiliary cylinder 26. The first elongated grooves 32 extend linearly and oppose each other with the central portion of the auxiliary cylinder 26 disposed therebetween.

A second elongated groove (locking mechanism) 33 is provided on the outer circumferential surface of the auxiliary cylinder 26 so as to extend from a mid-position L1 of the longitudinal direction of the first elongated grooves 32 along a direction perpendicular to the longitudinal direction. The second elongated groove 33 is formed over the entire circumference of the auxiliary cylinder section 26. A pair of recessed portions 36 is provided to recess toward the base end of the auxiliary cylinder section 26 at mid-positions L2 of the circumferential direction of the second elongated groove 33 and between the pair of the first elongated grooves 32. The recessed portions 36 oppose each other with the central portion of the auxiliary cylinder section 26 disposed therebetween.

The protruding portion 22 is provided in each of the first elongated grooves 32. The protruding portions 22 are moved relatively in the first elongated grooves 32. Accordingly, the auxiliary cylinder section 26 is supported to be reciprocatable in the axial direction of the support cylinder section 16. The reciprocating directions of the reciprocating movement of the auxiliary cylinder section 26 correspond to the longitudinal direction of the first elongated grooves 32.

As illustrated in FIG. 3, a base end flange 30 is formed in the base end of the auxiliary cylinder section 26. An outer diameter of the base end flange 30 is larger than an inner diameter of the tip flange 27. Since the base end flange 30 contacts the tip flange 27, the auxiliary cylinder section 16 is prevented from falling out of the support cylinder section 16. A tip flange 31 is provided at an end portion of the auxiliary cylinder section 26.

A main needle section 37 is provided in the inside of the support cylinder 16 and the auxiliary cylinder 26 to be coaxial with the support cylinder 16 and the auxiliary cylinder 26. The longitudinal dimension of the main needle section 37 is longer than those of the support cylinder 16 and the auxiliary cylinder 26. Thus, an end portion of the main needle section 37 protrudes from the tip flange 27 of the support cylinder 16.

The main needle section 37 is supported in the support cylinder 16 to be movable in the axial direction thereof. The main needle section 37 includes a bottomed cylindrical contour section 45 and a cylindrical core section 46. The core section 46 is inserted in the contour section 45. The core section 46 is supported to be reciprocatable along the axial direction thereof.

The contour section 45 includes a narrow diameter section 45a and an enlarged diameter section 45b provided at a base end of the narrow diameter section 45a. The narrow diameter section 45a and the enlarged diameter section 45b are formed integrally with each other. A step portion 50 is formed on an inner circumferential surface of the narrow diameter section 45a.

A step portion 51 is formed on an outer circumferential surface of the core section 46. The step portions 50 and 51 contact each other to prevent the core section 46 from falling out of the tip of the contour section 45.

A female screw portion, which is not shown, is formed at the tip of the core section 46 so as to extend toward a rear end of the core section 46. A cylindrical tip (contacting section) 40 is provided at the tip of the main needle section 37. A male screw portion, which is not shown, is provided on a rear end face of the tip 40. The male screw portion is screwed in the female screw portion of the core section 46. In this manner, the tip 40 is removably attached to the tip of the main needle section 37. The tip 40 can be replaced with other tips with the same diameter. Sanitary conditions can therefore be improved by the replacement of the tips.

A second pressure sensor 53 of, for example, a semiconductor, is provided inside of an enlarged diameter section 45b. When the tip 40 is pressed, the core section 46 is moved toward the rear side with respect to the contour section 45. The second pressure sensor 53 measures the pressure of the core section 46 at this time.

A first pressure sensor 54 is provided at the rear side of the second pressure sensor 53 and on an outer bottom surface of the enlarged diameter section 45b. When the auxiliary cylinder 26 and the tip 40 are pressed, the main needle section 37 is moved backward with respect to the support cylinder 16. The first pressure sensor 54 measures the pressure of the main needle section 37 at this time.

A coil spring 43 is provided on an outer circumference of the main needle section 37. That is, the main needle section 37 is inserted in the inside the coil spring 43. A longitudinal dimension of the coil spring 43 (in its not elastically deformed state) is larger than a longitudinal dimension of the narrow diameter portion 45a. An inner diameter of the coil spring 43 is larger than an outer diameter of the enlarged diameter section 45b and the inner diameter of the tip flange 31. That is, the coil spring 43 is disposed between the distal end surface of the enlarged diameter section 45b and the inner surface of the tip flange 31. Accordingly, the auxiliary cylinder 26 is always urged toward the tip. The base end flange 30 contacts the tip flange 27 to keep the auxiliary cylinder 26 protruding from the tip of the support cylinder 16.

In a natural state with no external force being applied, a distal end surface (second contact surface) 26a of the auxiliary cylinder 26 is coplanar with a distal end surface (first contact surface) 40a of the tip 40. The position at which the auxiliary cylinder 26 is disposed at this time will be referred to as a coplanar position P1.

Figure 5:
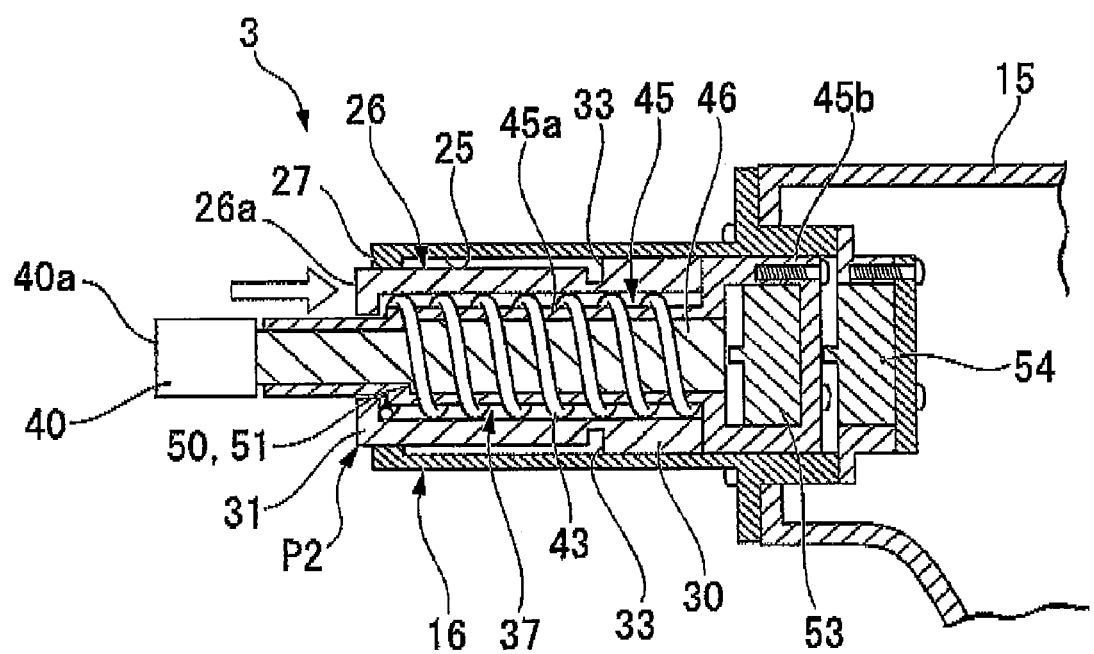
FIG. 5 is a lateral cross-sectional view illustrating a part of the probe of the living body measurement apparatus illustrated in FIG. 1 in a state in which the auxiliary cylinder is disposed at a retracted position.

When the auxiliary cylinder 26 is pressed toward the base end, as illustrated in FIG. 5, the auxiliary cylinder 26 is moved in a direction to be pushed into the support cylinder 16 against the urging force of the coil spring 43. At this time, the protruding portion 22 is moved relatively in the first elongated groove 32. In a state in which the protruding portion 22 is disposed at the mid-position L1, the auxiliary cylinder 26 is made to rotate about the axis of the auxiliary cylinder 26. In this manner, the protruding portion 22 is disposed in the second elongated groove 33 and is moved relatively in the second elongated groove 33. With the protruding portion 22 being disposed at the mid-position L2, the auxiliary cylinder 26 is released (i.e., the user releases his or her hand). Since the auxiliary cylinder 26 is urged forward by the urging force of the coil spring 43, the auxiliary cylinder 26 is moved forward. As a result, the protruding portion 22 is disposed in the recessed portion 36. In this manner, the auxiliary cylinder 26 is kept in a position pushed into the support cylinder 16. At this time, the distal end surface 26a of the auxiliary cylinder 26 is disposed at a position retracted from the distal end surface 40a of the tip 40. The position at which the auxiliary cylinder 26 is disposed at this time will be referred to as a retracted position P2.

Next, function groups of the living body measurement apparatus 1 according to the present embodiment will be described.

Figure 6:
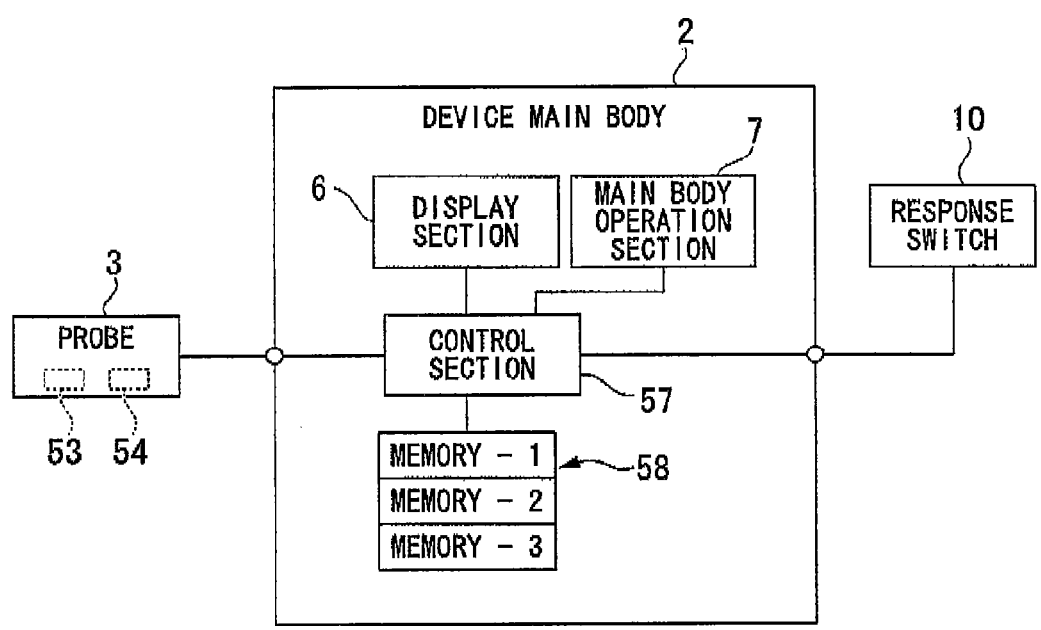
FIG. 6 is a block diagram illustrating function groups of the living body measurement apparatus illustrated in FIG. 1.

FIG. 6 is a block diagram illustrating function groups of the living body measurement apparatus 1.

The device main body 2 includes a control section 57 which controls the entire device. The display section 6 and the main body operation section 7 are connected to the control section 57.

The second pressure sensor 53 and the first pressure sensor 54 in the probe 3 are connected to the control section 57. The response switch 10 is connected to the control section 57. A memory 58 for storing various information is connected to the control section 57. Thresholds regarding pressing pressure of the first pressure sensor 54 are previously stored in the memory 58.

With this configuration, when measurement signals are output from the second pressure sensor 53 and the first pressure sensor 54, the control section 57 reads the measurement signals. Measurement value information obtained through predetermined calculation on the basis of the measurement signals is displayed sequentially on the display section 6. Moreover, the control section 57 stores the predetermined measurement value information in the memory 58. When response signals are output from the response switch 10, the control section 57 reads the response signals and drives the display section 6. That is, the control section 57 makes the response information displayed on the display section 6.

Next, an operation of the thus-configured living body measurement apparatus 1 according to the present embodiment will be described.

A user operates the main body operation section 7 to previously store the thresholds regarding the first pressure sensor 54 in the memory 58.

Figure 7:
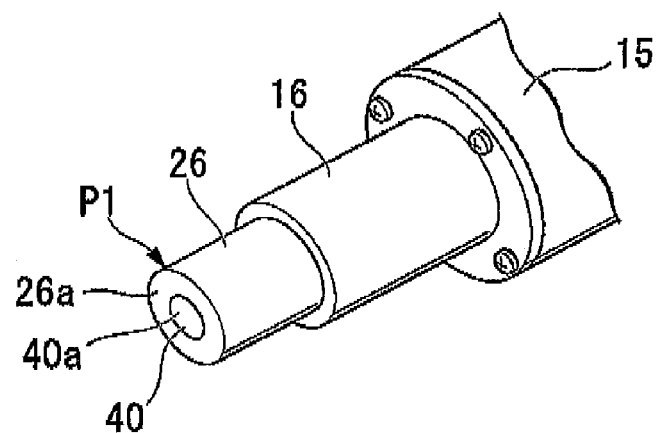
FIG. 7 is a perspective view illustrating the living body measurement apparatus illustrated in FIG. 1 used as a muscular tissue hardness tester in a state in which the auxiliary cylinder is disposed at a coplanar position.

When the living body measurement apparatus 1 is used as a muscular tissue hardness tester, as illustrated in FIG. 7, the auxiliary cylinder 26 is first disposed at the coplanar position P1. The distal end surface 40a of the tip 40 and the distal end surface 26a of the auxiliary cylinder 26 are then made to contact a subject site and the living body measurement apparatus 1 is made to be pushed against it.

In this manner, the distal end surface 26a of the auxiliary cylinder 26 applies a tension to the skin. In this state, the tip 40 is pushed against the skin. At this time, owing to the reaction, a pressing pressure is applied backward with respect to the tip 40 and the auxiliary cylinder 26.

The pressing pressure with respect to the tip 40 is directly applied to the main needle section 37. That is, the pressing pressure with respect to the tip 40 is applied to the core section 46. Accordingly, the core section 46 moves backward with respect to the contour section 45. As a result, the pressing pressure with respect to tip 40 is applied to the second pressure sensor 53. At this time, the second pressure sensor 53 outputs measurement signals in accordance with the pressing pressure. The pressing pressure with respect to the second pressure sensor 53 is applied to the contour section 45.

At the same time, the pressing pressure with respect to the auxiliary cylinder 26 is indirectly applied to the main needle section 37 via the coil spring 43. As a result, the main needle section 37 is moved backward with respect to the support cylinder 16 and the pressing pressure is applied to the first pressure sensor 54. At this time, the first pressure sensor 54 outputs measurement signals in accordance with the pressing pressure.

The control section 57 reads the measurement signals output from the second pressure sensor 53 and the first pressure sensor 54 and makes the measurement value information be displayed sequentially on the display section 6. The control section 57 reads the threshold information stored in the memory 58 and compares the threshold information with the measurement value information regarding the first pressure sensor 54. When the control section 57 determines that the measurement value information regarding the first pressure sensor 54 exceeds the threshold information, the control section 57 stores the measurement value information regarding the second pressure sensor 53 at that time in the memory 58.

In this manner, hardness of muscular tissue is measured and stored.

Figure 8:
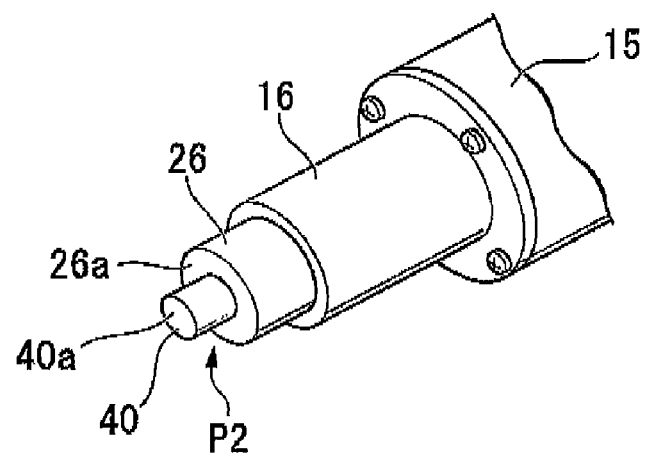
FIG. 8 is a perspective view illustrating the living body measurement apparatus illustrated in FIG. 1 used as an algesiometer shown in the state in which the auxiliary cylinder is disposed at the retracted position.

On the other hand, when the living body measurement apparatus 1 is used as an algesiometer, as illustrated in FIG. 8, the auxiliary cylinder 26 is disposed and locked at the retracted position P2. In this manner, the tip 40 is made to protrude from the distal end surface 26a of the auxiliary cylinder 26. The subject is asked to hold the response switch 10. In this state, the tip 40 is made to contact the subject site and the living body measurement apparatus 1 is made to be pushed against it.

As a result, owing to the reaction, a pressing pressure is applied backward with respect to the tip 40.

The pressing pressure with respect to the tip 40 is directly applied to the core section 46. Accordingly, the core section 46 is moved backward with respect to the contour section 45 and the pressing pressure is applied to the second pressure sensor 53.

At this time, the second pressure sensor 53 outputs measurement signals in accordance with the pressing pressure. Then, the control section 57 reads the measurement signals and makes the measurement value information be sequentially displayed on the display section 6. When the subject feels pain, he or she presses the response switch 10. Then, response signals are output from the response switch 10. The control section 57 reads the response signals and makes the response information be displayed on the display section 6. The response information is displayed with characters or figures. At the same time, the control section 57 stores the measurement value information when the response signals are read out in the memory 58.

In this manner, the degree of sense of pain is measured and stored.

In order to release the lock of the auxiliary cylinder 26, the auxiliary cylinder 26 is first pushed backward so that the protruding portion 22 is disposed at the mid-position L2. Next, the auxiliary cylinder 26 is made to rotate about the axis of the auxiliary cylinder 26. In this manner, the protruding portion 22 is relatively moved in the second elongated groove 33. Next, when the protruding portion 22 is disposed at the mid-position L1, the auxiliary cylinder 26 is released. The auxiliary cylinder 26 is then pushed forward by the urging force of the coil spring 43 and the protruding portion 22 is moved relatively in the first elongated groove 32. As a result, the auxiliary cylinder 26 is kept at the coplanar position P1.

As described above, with the living body measurement apparatus 1 according to the present embodiment, the auxiliary cylinder 26 can be locked at the retracted position P2. Accordingly, hardness of the muscular tissue and the degree of sense of pain can be measured easily and highly accurately with a single device.

A single apparatus functions both as the muscular tissue hardness tester and the algesiometer. Accordingly, the control burden of the device can be reduced.

The first elongated groove 32, the second elongated groove 33 and the protruding portion 22 are provided. Accordingly, the auxiliary cylinder 26 can be securely locked with a simple structure.

Since the recessed portions 36 are provided, it is possible to reliably keep a locked state.

Since the response switch 10 is provided, a measurer can be promptly reported of the moment the subject felt pain. With this configuration, the degree of sense of pain of the subject can be measured with high accuracy. Since the measurement value information is stored in accordance with the response signals of the response switch 10, the measurement can be made easily and highly accurately.

If the subject is asked to verbally report the moment he or she feels the pain, there should be a time-lag between the moment he or she feels the pain and the moment he or she utters a voice. Accordingly, it is difficult to make an accurate measurement. If the subject is asked to tell by body movements, there should also be a time-lag between the moment at which the measurer confirms the body movements and the moment the measurer looks display on the display section 6. Accordingly, it is also difficult to make an accurate measurement.

With the living body measurement apparatus 1 according to the present embodiment, the subject can easily report by easy operation of pressing the response switch 10. Accordingly, a highly accurate measurement can be made.

Figure 9:
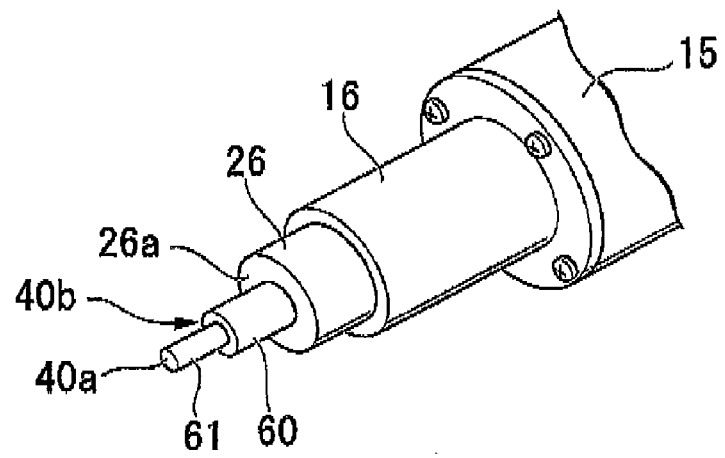
FIG. 9 is a perspective view illustrating a first modified example of a tip of the living body measurement apparatus illustrated in FIG. 1.
Figure 10:
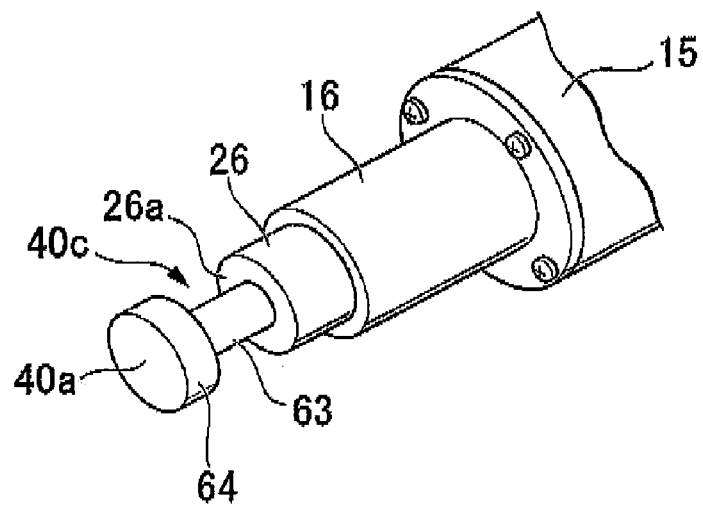
FIG. 10 is a perspective view illustrating a second modified example of the tip of the living body measurement apparatus illustrated in FIG. 1.

Although only one kind of a tip 40 is described in the foregoing embodiment, the invention is not limit thereto. Several kinds of tips of varying sizes may be prepared and these tips of varying sizes may be replaced selectively. The term "size" does not only mean the dimension but mean the configuration and the like. For example, as illustrated in FIG. 9, it is possible to attach a tip 40b in which a narrow diameter section 61 is provided at the tip of a cylindrical enlarged diameter section 60. As illustrated in FIG. 10, it is also possible to attach a tip 40c in which an enlarged diameter section (disk section) 64 is provided at the tip of a cylindrical narrow diameter section 63. As described above, by attaching an optimal tip in accordance with the state of the subject site, a further accurate measurement can be made.

In the foregoing embodiment, the first elongated groove 32 and the second elongated groove 33 are provided in the auxiliary cylinder 26 and the protruding portion 22 is provided in the support cylinder 16. Alternatively, however, the protruding portion 22 may be provided in the auxiliary cylinder 26 and the first elongated groove 32 and the second elongated groove 33 may be provided in the support cylinder 16.

Although the recessed portions 36 are provided, they may be omitted. That is, only the protruding portion 22 being disposed in the second elongated groove 33 can lock the auxiliary cylinder 26. However, it is preferred that the recessed portions 36 be provided since it is possible to reliably keep the locked state.

Although the response switch 10 is provided, it may be omitted. However, it is preferred that the response switch 10 be provided since a highly accurate measurement can be made.

Although the response of the response switch 10 is notified through the display section 6, it is not limited thereto and various modifications may be made. For example, the response may be notified by sound or vibration.

The technical range of the invention is not limited to the foregoing embodiment and various modifications may be made without departing from the spirit and scope of the invention.

INDUSTRIAL APPLICABILITY

The invention can be applied to a living body measurement apparatus for measuring hardness of a muscular tissue and the degree of sense of pain of a living body. According to the living body measurement apparatus, the hardness of the muscular tissue and the degree of sense of pain can be measured easily and highly accurately with a single device.

The invention claimed is:

1. A living body measurement apparatus which functions both as a muscular tissue hardness tester for measuring hardness of muscular tissue of a living body and as an algesiometer for measuring a degree of sense of pain of the living body, the apparatus comprising:
    a contacting section which includes a first contact surface configured to contact the living body, the contacting section configured to apply pressure to the living body;
    an auxiliary section which includes a second contact surface configured to contact the living body, and the auxiliary section configured to support the second contact surface so that the second contact surface performs reciprocating movement between a coplanar position in which the second contact surface is disposed substantially coplanar with the first contact surface and a retracted position in which the second contact surface is retracted with respect to the first contact surface, the auxiliary section being provided outside of the contacting section;
    a first pressure sensor which is configured to measure pressure applied to both of the contacting section and the auxiliary section;
    a second pressure sensor which is configured to measure pressure applied only to the contacting section, the second pressure sensor configured to apply the pressure applied only to the contacting section to the first pressure sensor by pressing the first pressure sensor;
    a support section which is configured to support the auxiliary section so that the second contact surface performs the reciprocating movement; and
    a locking mechanism including:
    a first elongated groove which is formed in either one of the auxiliary section and the support section, and which extends in a reciprocating direction of the reciprocating movement of the second contact surface;
    a second elongated groove which is formed in the one of the auxiliary section and the support section, and which extends from a mid-position of the first elongated groove in a direction perpendicular to the reciprocating direction,
    a recessed portion which is formed at a mid-position of the second elongated groove, and
    a protruding portion which is formed in the other of the auxiliary section and the support section, and which is disposed at either one of the first elongated groove, the second elongated groove and the recessed portion,
    the auxiliary section configured to rotate about an axis of the auxiliary section in a state in which the protruding portion is disposed at the second elongated groove or at the mid-position of the first elongated groove, so that the protruding portion moves in the second elongated groove,
    the locking mechanism configured to lock the auxiliary section in a state in which the second contact surface is disposed at the retracted position by disposing the protruding portion in the recessed portion,
    wherein the living body measurement apparatus functions as the muscular tissue hardness tester in a state in which the second contact surface is disposed at the coplanar position, both of the first and second contacting surfaces are configured to contact the living body, and both of the contacting section and the auxiliary section are configured to apply pressure to the living body, and
    the living body measurement apparatus functions as the algesiometer in a state in which the second contact surface is disposed at the retracted position, only the first contacting surface is configured to contact the living body, and only the contacting section is configured to apply pressure to the living body by the locking mechanism locking the auxiliary section.

2. The living body measurement apparatus according to claim 1, further comprising:
    a response operating section which is configured to output a response signal;
    a reporting section which is configured to report output of the response signal; and
    a control section which is configured to perform control of driving the reporting section when the response signal is input from the response operating section.

3. The living body measurement apparatus according to claim 1, wherein the contacting section is replaceable.

4. The living body measurement apparatus according to claim 1, wherein the first pressure sensor is aligned with the second pressure sensor in the reciprocating direction, the first pressure sensor is provided at a rear side of the second pressure sensor, and the first pressure sensor is configured to measure pressure applied to the contacting section by the second pressure sensor moving toward the rear side of the second pressure sensor.

5. The living body measurement apparatus according to claim 1, further comprising:
    a contour section in side of which the second pressure sensor is provided, the first pressure sensor provided outside of the contour section, wherein the second pressure sensor is configured to apply the pressure applied only to the contacting section by pressing the contour section.

6. The living body measurement apparatus according to claim 5, further comprising:
    a spring which is configured to contact both of the auxiliary section and the contour section, and apply pressure applied only to the auxiliary section to the contour section.

* * * * *